(12) United States Patent
Alasmary et al.

(10) Patent No.: US 12,234,205 B1
(45) Date of Patent: Feb. 25, 2025

(54) SULFONYLHYDRAZIDE DERIVATIVES AS ANTICANCER AGENTS

(71) Applicant: KING SAUD UNIVERSITY, Riyadh (SA)

(72) Inventors: Fatmah Ali S. Alasmary, Riyadh (SA); Moustafa E. El-Araby, Riyadh (SA); Linah Saad N. Alqahtani, Riyadh (SA); Amr M. El-Araby, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/671,935

(22) Filed: May 22, 2024

(51) Int. Cl.
| | |
|---|---|
| *C07C 317/48* | (2006.01) |
| *A61K 31/18* | (2006.01) |
| *A61K 31/381* | (2006.01) |
| *A61K 31/4406* | (2006.01) |
| *A61P 31/00* | (2006.01) |
| *C07D 213/78* | (2006.01) |
| *C07D 333/34* | (2006.01) |

(52) U.S. Cl.
CPC ............ *C07C 317/48* (2013.01); *A61K 31/18* (2013.01); *A61K 31/381* (2013.01); *A61K 31/4406* (2013.01); *A61P 31/00* (2018.01); *C07D 213/78* (2013.01); *C07D 333/34* (2013.01)

(58) Field of Classification Search
CPC . A61P 35/00; C07C 2601/02; C07C 2601/04; C07C 327/56; C07C 333/12; C07C 335/40; C07C 337/02; C07C 337/06; C07D 211/72; C07D 213/86; C07D 213/87; C07D 241/24; C07D 277/56; C07D 295/155; C07D 295/195; C07D 307/68; C07D 317/68; C07D 333/38; C07D 333/68
See application file for complete search history.

(56) References Cited

U.S. PATENT DOCUMENTS

| | | |
|---|---|---|
| 6,420,409 B1 | 7/2002 | Yamasaki et al. |
| 8,153,814 B2 | 4/2012 | Beaudoin et al. |
| 8,664,253 B2 | 3/2014 | Liu et al. |
| 9,353,082 B2 | 5/2016 | Kiss et al. |
| 2009/0137603 A1 | 5/2009 | Nara et al. |

FOREIGN PATENT DOCUMENTS

JP    2005-298627 A    10/2005

OTHER PUBLICATIONS

Alsaif, "Design, Synthesis and in vitro evaluation of derivatives of nonsteroidal anti-inflammatory drugs as inhibitors of fatty acid amide hydrolase," PhD Thesis, MCPHS University, 2017.
Tripathi, "A perspective review on fatty acid amide hydrolase (FAAH) inhibitors as potential therapeutic targets," European Journal of Medicinal Chemistry, vol. 188, Feb. 15, 2020.
Shang et al., "Discovery of heterocyclic carbohydrazide derivatives as novel selective fatty acid amide hydrolase inhibitors: design, synthesis and anti-neuroinflammatory evaluation," Bioorganic & Medicinal Chemistry Letters, vol. 30, Issue 10, May 15, 2020.

*Primary Examiner* — Savitha M Rao
(74) *Attorney, Agent, or Firm* — Nath, Goldberg & Meyer; Joshua B. Goldberg

(57) ABSTRACT

Novel sulfonylhydrazide derivatives, a method of synthesizing said compounds, a pharmaceutical composition comprising said compounds and a suitable carrier, and a method of using the compounds. The sulfonylhydrazide derivative compounds, identified as FAAH inhibitors, are useful as anticancer and/or antitumor agents.

8 Claims, 1 Drawing Sheet

SULFONYLHYDRAZIDE DERIVATIVES AS ANTICANCER AGENTS

BACKGROUND

1. Field

The present disclosure provides novel sulfonylhydrazide derivatives that inhibit fatty acid amide hydrolase (FAAH) activity, compositions containing such compounds, and methods of their preparation. These compounds and compositions are useful as therapeutic agents for treating proliferative disorders such as cancer.

2. Description of the Related Art

Fatty acid amide hydrolase (FAAH) degrades fatty acid amides like oleamide to terminate CB1 and CB2 signaling in the central nervous system. The involvement of FAAH in tumor proliferation provides an opportunity to discover FAAH inhibitors as anticancer agents.

Fatty Acid Amide Hydrolase (FAAH) is a serine-dependent hydrolyzing enzyme encompassing both esterase and amidase activities. FAAH is present as a dimer bound to the endoplasmic reticulum and it is responsible for the hydrolysis and termination of the biochemical activities of a number of lipid mediators such as N-arachidonyl ethanolamine (AEA). AEA is an endocannabinoid that shows a partial agonist activity on cannabinoid CB-1 receptors with an affinity comparable to $\Delta^9$-tetrahydrocannabinol (THC) while being inactive against CB-2 receptors. It has been shown in a number of previous reports that AEA possesses pro-apoptotic and cytotoxic effects. For this reason, under normal physiological conditions, AEA levels are closely regulated and controlled. However, in cancer cell environment, FAAH is found to be overexpressed to maintain lowered AEA levels and overcome the cytotoxic effects of this molecule. Due to this phenomenon, FAAH inhibitors have been investigated as potential anticancer agents. Indeed, such an approach was proven effective in vitro against a number of cancer cell lines, nonetheless, activity did vary according to the type of cell line. Examples of cell lines that were effectively inhibited by FAAH inhibitors were CaCo-2 colorectal cells, Colo-205 colon adenocarcinoma cells, non-small cell lung cancer cell line A549 and prostate cancer cell line LNCaP.

Drug Repurposing (aka Drug Repositioning) is a common tool that has been widely utilized to introduce novel uses of existing drugs. Drug Repurposing has become intensely employed in searching for a rapid development of effective remedies of Covid-19 pandemic. Meanwhile, another related approach may use existing drugs scaffolds as pharmacophoric entities in designing compounds that bind to different targets and, therefore, elicit different pharmacological actions. This approach, can be generically designated (although no precedent in literature found) as "Semi-Repurposing". The semi-repurposing of existing drugs has certain advantages such as potential safety because such pharmacophores have been widely and safely prescribed and consumed by humans.

NSAIDs are non-selective cyclooxygase 1&2 inhibitors commonly administeredy in patients of all ages, genders, and underlying conditions for decades mainly to combat pain and inflammatory disorders. FAAH inhibitors have also been studied for their synergistic effect on NSAIDs. These compounds potentiate NSAIDs analgesic activity and help in the modulation of their side effects. Another motivating correlation between NSAIDs and FAAH is that literature reports provide strong evidence that NSAIDs are able to bind to and inhibit FAAH. As an example, carprofen was utilized as a pharmacophore to design dual FAAH/Cox1&2 inhibitors, although the authors met only limited success. A binding site for NSAIDs in the FAAH enzyme has been also reported and this can be attributed to the fact that both oxygenases (NSAID known targets) and FAAH utilize fatty acids as substrates. These findings provide a unique opportunity for the semi-repurposing of clinically safe NSAIDs into FAAH inhibitors by derivatization.

Thus, new antitumoral/anti-cancer compounds solving the aforementioned problems are desired.

SUMMARY

The present subject matter relates to semi-repurposing approach that is embarked on ibuprofen by structure-based design of arylsulfonhydrazide derivatives of potent FAAH inhibitors.

Ibuprofen was preferred over other NSAID scaffolds for the virtue of high safety. The design hypothesis and structure-activity relationship (SAR) of the reported compounds was studied in silico using molecular docking experiments. The synthesized compounds were tested in vitro against FAAH and showed low nanomolar $IC_{50}$ values. Finally, to assess the anticancer properties of our compounds, cancer cell line inhibition assays were carried out against the FAAH-sensitive NSCLC cell line A549.

In an embodiment, the present subject matter relates to a compound having the formula I:

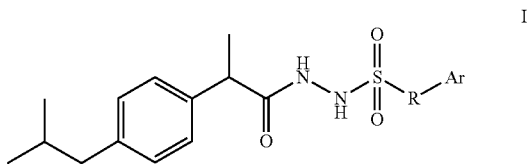

I or a pharmaceutically acceptable salt, ester, stereoisomer, or solvate thereof, wherein:
 R is a direct bond or —$CH_2$, or CH(Br);
 Ar is an aryl ring or a 5 or 6 membered heteroaryl ring, either of the aryl ring or the heteroaryl ring being optionally substituted with one or more substituents selected from the group consisting of hydrogen, halogen, $COCH_3$, $NO_2$, $CF_3$, $OCH_3$, $C_1$-$C_6$ straight chained alkyl, $C_1$-$C_6$ branched alkyl, $C_3$-$C_6$ cycloalkyl, methyl-$C_1$-$C_6$ cycloalkyl, methoxy-$C_1$-$C_6$ cycloalkyl, and cyano-$C_3$-$C_6$ cycloalkyl; wherein the heteroaryl rings contain nitrogen or sulfur.

In another embodiment, the present subject matter relates to a compound having the formula I:

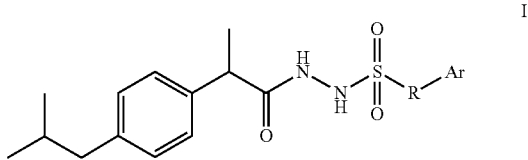

I or a pharmaceutically acceptable salt, ester, stereoisomer, or solvate thereof, wherein:

R is a direct bond, —$CH_2$, or —CH (Br);

Ar is an optionally substituted phenyl, pyridine, naphthalene, or thiophene being optionally substituted with one or more substituents selected from the group consisting of hydrogen, bromine, $COCH_3$, $NO_2$, $CF_3$, $OCH_3$, methyl, isopropyl, and a second optionally substituted phenyl;

wherein the second optionally substituted phenyl is substituted with a hydrogen, methyl, or methoxy.

In an embodiment, the present subject matter relates to a compound selected from the group consisting of: 4-acetyl-N'-(2-(4-isobutylphenyl)propanoyl)benzenesulfonohydrazide (1); N'-(2-(4-isobutylphenyl) propanoyl)-4-methylbenzene sulfonohydrazide (2); N'-(2-(4-isobutylphenyl) propanoyl)-2-nitrobenzenesulfonohydrazide (3); N'-(2-(4-isobutylphenyl)propanoyl)naphthalene-2-sulfonohydrazide (4); N'-(2-(4-isobutylphenyl) propanoyl)-2, 4, 6 triisopropyl benzene sulfonohydrazide (5); 1-bromo-N'-(2-(4-isobutylphenyl) propanoyl)-1-phenylmethane sulfonohydrazide (6); N'-(2-(4-isobutylphenyl) propanoyl)-3-(trifluoromethyl) benzene sulfonohydrazide (7); N'-(2-(4-isobutylphenyl) propanoyl)-4-(trifluoromethyl) benzene sulfonohydrazide (8); N'-(2-(4-isobutylphenyl) propanoyl) benzenesulfonohydrazide (9); N'-(2-(4-isobutylphenyl) propanoyl)-[1, 1'-biphenyl]-4-sulfonohydrazide (10); N'-(2-(4-isobutylphenyl) propanoyl)-4'-methyl-[1, 1'-biphenyl]-4-sulfonohydrazide (11); N'-(2-(4-isobutylphenyl) propanoyl)-4'-methoxy-[1, 1'-biphenyl]-4sulfonohydrazide (12); 4-Bromo-N'-(2-(4-isobutylphenyl)propanoyl)benzenesulfonohydrazide (13); N'-(2-(4-isobutylphenyl) propanoyl)-3, 4-dimethoxybenzene sulfonohydrazide (14); N'-(2-(4-isobutylphenyl)propanoyl)thiophene-2-sulfonohydrazide (15); 5-bromo-N'-(2-(4-isobutylphenyl) propanoyl) thiophene-2-sulfonohydrazide (16); N'-(2-(4-isobutylphenyl)propanoyl)-5-methylthiophene-2-sulfonohydrazide (17); N'-(2-(4-isobutylphenyl)propanoyl)pyridine-3-sulfonohydrazide (18); N'-(2-(4-isobutylphenyl) propanoyl)-6-(trifluoromethyl)pyridine-3sulfonohydrazide (19); N'-(2-(4-isobutylphenyl)propanoyl)-1-phenylmethanesulfonohydrazide (20); and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of inhibiting FAAH enzyme activity and of treating various cancers by administering the present compounds to a patient in need thereof.

These and other features of the present subject matter will become readily apparent upon further review of the following specification.

DETAILED DESCRIPTION OF THE PREFERRED EMBODIMENTS

Figure 1:
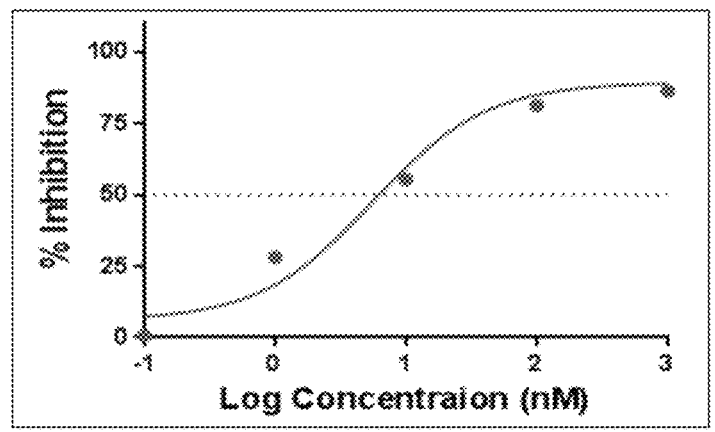
FIG. 1 shows a graph of inhibition of hFAAH by compound 10 as described herein.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_3M$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules.

All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cancer.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

NSAIDs are non-selective cyclooxygenase 1 and 2 inhibitors commonly administered to patients of all ages, genders and underlying conditions for decades mainly to combat pain and inflammatory disorders. FAAH inhibitors have also been studied for their synergistic effect on NSAIDs. These compounds potentiate NSAIDs analgesic activity and help in the modulation of their side effects. Another motivating correlation between NSAIDs and FAAH is that literature reports provide strong evidence that NSAIDs are able to bind to and inhibit FAAH.

As an example, carprofen was utilized as a pharmacophore to design dual FAAH/Cox1&2 inhibitors, although the authors met only limited success. A binding site for NSAIDs in the FAAH enzyme has been also reported and this can be attributed to the fact that both oxygenases (NSAID known targets) and FAAH utilize fatty acids as substrates. These findings provide a unique opportunity for the semi-repurposing of clinically safe NSAIDs into FAAH inhibitors by derivatization.

In an embodiment, the present subject matter relates to a compound having the formula I:

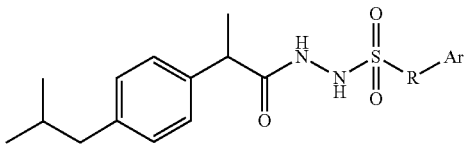

or a pharmaceutically acceptable salt, ester, stereoisomer, or solvate thereof, wherein:
R is a direct bond or —$CH_2$, or CH (Br);
Ar is an aryl ring or a 5 or 6 membered heteroaryl ring, either of the aryl ring or the heteroaryl ring being optionally substituted with one or more substituents selected from the group consisting of hydrogen, halogen, $COCH_3$, $NO_2$, CF3, $OCH_3$, $C_1$-$C_6$ straight chained alkyl, $C_1$-$C_6$ branched alkyl, $C_3$-$C_6$ cycloalkyl, methyl-$C_1$-$C_6$ cycloalkyl, methoxy-$C_1$-$C_6$ cycloalkyl, and cyano-$C_3$-$C_6$ cycloalkyl;
wherein the heteroaryl rings contain nitrogen or sulfur.

In a further embodiment, the present subject matter relates to compounds of formula I, wherein R is an optionally substituted —Ar group.

In yet another embodiment, the present subject matter relates to compounds of formula I, wherein R may be -phenyl substituted with one or more substituents independently selected from the group consisting of hydrogen, —$COCH_3$, a straight or branched $C_1$-$C_6$ alkyl, an optionally substituted $C_3$-$C_6$ cycloalkyl, —$NO_2$, $CF_3$, bromine, and —$OCH_3$. The optionally substituted $C_3$-$C_6$ cycloalkyl may be a phenyl substituted with a methyl or a phenyl substituted with a methoxy. The straight chained $C_1$-$C_6$ alkyl may be a methyl or three isopropyl groups.

In another embodiment, the present subject matter relates to a compound of formula I, wherein Ar is an optionally substituted pyridine substituted with $CF_3$.

In an embodiment the present subject matter relates to compounds of formula I, R is an optionally substituted thiophene. In various embodiments, the thiophene may be substituted with a methyl or a bromine.

In another embodiment, the present subject matter relates to a compound having the formula I:

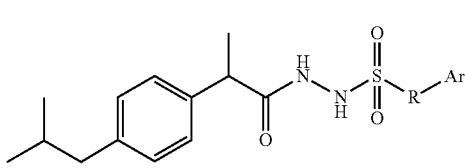

or a pharmaceutically acceptable salt, ester, stereoisomer, or solvate thereof, wherein:
R is a direct bond, —$CH_2$, or —$CH_2$ (Br);
Ar is an optionally substituted phenyl, pyridine, naphthalene, or thiophene being optionally substituted with one or more substituents selected from the group consisting of hydrogen, bromine, $COCH_3$, $NO_2$, $CF_3$, $OCH_3$, methyl, isopropyl, and a second optionally substituted phenyl;
wherein the second optionally substituted phenyl is substituted with a hydrogen, methyl, or methoxy.

In an embodiment, the present subject matter relates to a compound selected from the group consisting of: 4-acetyl-N'-(2-(4-isobutylphenyl)propanoyl)benzenesulfonohydrazide (1); N'-(2-(4-isobutylphenyl) propanoyl)-4-methylbenzene sulfonohydrazide (2); N'-(2-(4-isobutylphenyl) propanoyl)-2-nitrobenzenesulfonohydrazide (3); N'-(2-(4-isobutylphenyl)propanoyl)naphthalene-2-sulfonohydrazide (4); N'-(2-(4-isobutylphenyl) propanoyl)-2, 4, 6 triisopropyl benzene sulfonohydrazide (5); 1-bromo-N'-(2-(4-isobutylphenyl) propanoyl)-1-phenylmethane sulfonohydrazide (6); N'-(2-(4-isobutylphenyl) propanoyl)-3-(trifluoromethyl) benzene sulfonohydrazide (7); N'-(2-(4-isobutylphenyl) propanoyl)-4-(trifluoromethyl) benzene sulfonohydrazide (8); N'-(2-(4-isobutylphenyl) propanoyl) benzenesulfonohydrazide (9); N'-(2-(4-isobutylphenyl) propanoyl)-[1, 1'-biphenyl]-4-sulfonohydrazide (10); N'-(2-(4-isobutylphenyl) propanoyl)-4'-methyl-[1, 1'-biphenyl]-4-sulfonohydrazide (11); N'-(2-(4-isobutylphenyl) propanoyl)-4'-methoxy-[1, 1'-biphenyl]-4sulfonohydrazide (12); 4-Bromo-N'-(2-(4-isobutylphenyl)propanoyl)benzenesulfonohydrazide (13); N'-(2-(4-isobutylphenyl) propanoyl)-3, 4-dimethoxybenzene sulfonohydrazide (14); N'-(2-(4-isobutylphenyl)propanoyl)thiophene-2-sulfonohydrazide (15); 5-bromo-N'-(2-(4-isobutylphenyl) propanoyl) thiophene-2-sulfonohydrazide (16); N'-(2-(4-isobutylphenyl)propanoyl)-5-methylthiophene-2-sulfonohydrazide (17); N'-(2-(4-isobutylphenyl)propanoyl)pyridine-3-sulfonohydrazide (18); N'-(2-(4-isobutylphenyl)propanoyl)-6-(trifluoromethyl)pyridine-3sulfonohydrazide; N'-(2-(4-isobutylphenyl)propanoyl)-1-phenylmethanesulfonohydrazide (20); and a pharmaceutically acceptable salt, ester, stereoisomer, or solvate thereof.

Said differently, the present subject matter can relate to compounds of formula I selected from the group consisting of:

1

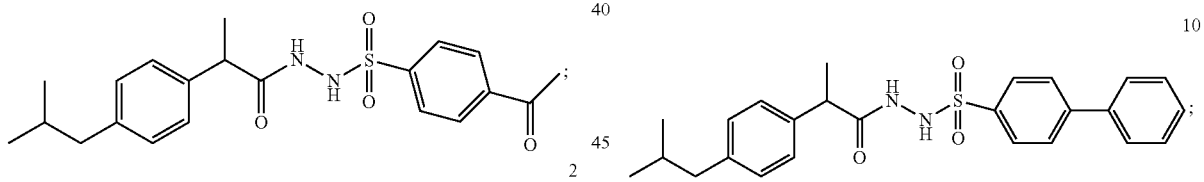

2

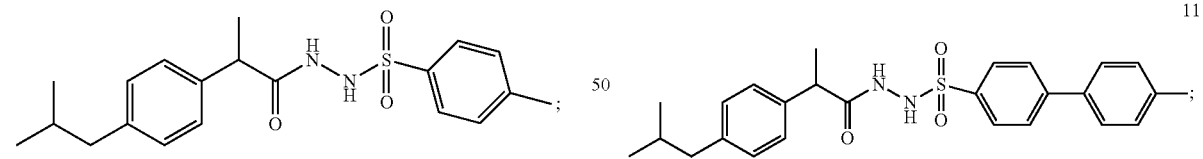

3

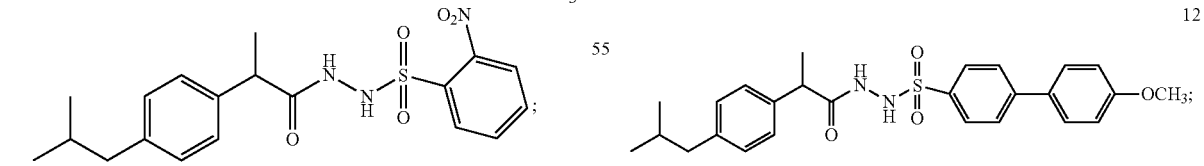

4

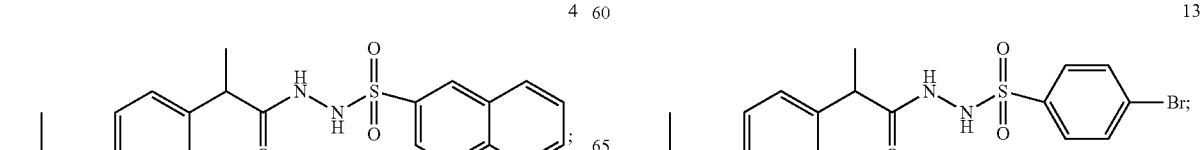

5

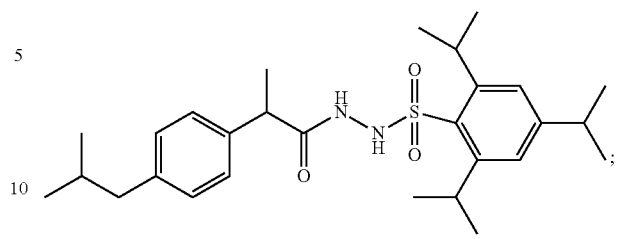

6

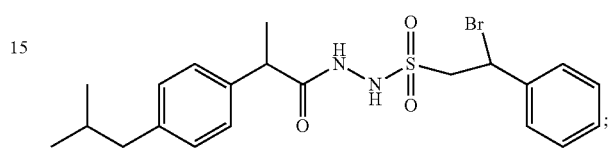

7

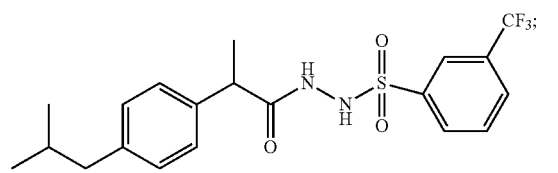

8

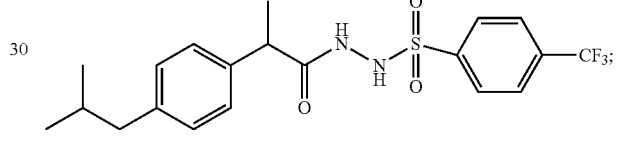

9

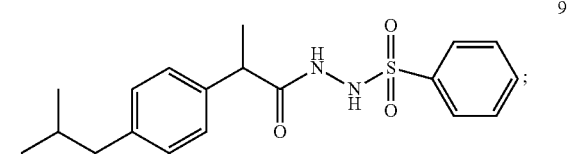

10

11

12

13

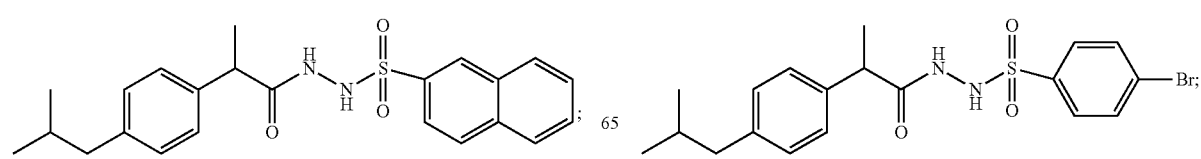

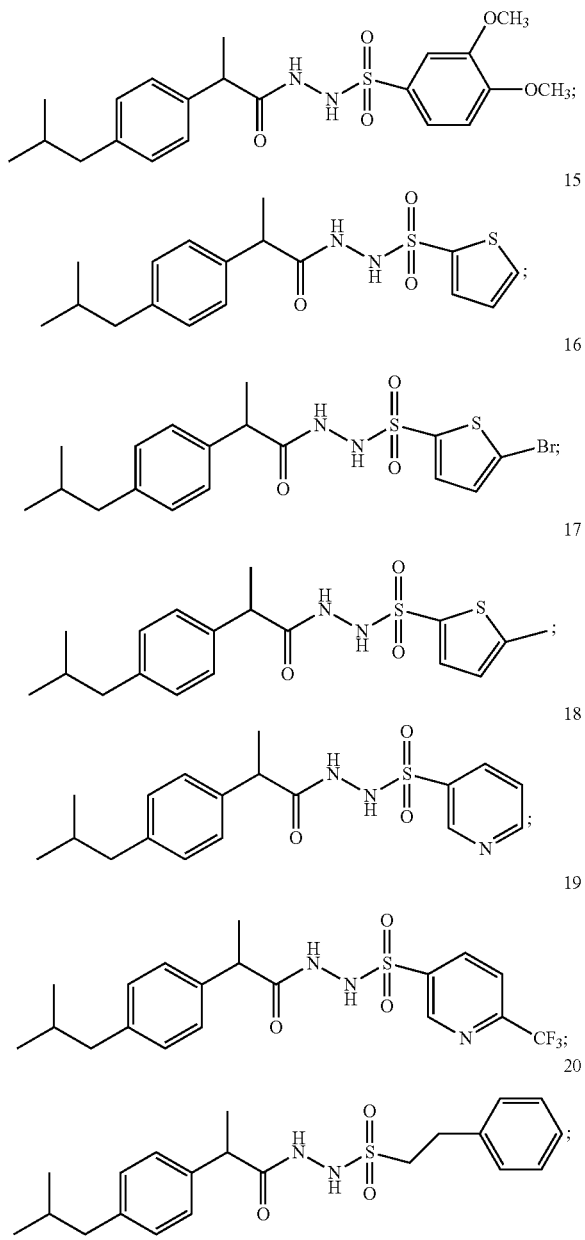

and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. Specifically, synthesis commences with esterification of ibuprofen to yield the ibuprofen ethyl ester ethyl 2-(4-isobutylphenyl) propanoate (1). This ester can then be reacted with hydrazine hydrate to yield 2-(4-isobutylphenyl) propanehydrazide (2) according to synthetic procedures in previous literature. Finally, ibuprofen arylsulfonhyrazides can be synthesized via a nucleophilic substitution reaction between the hydrazide compound 2 and arylsulfonylchloride derivatives 3a-t yielding the target compounds as illustrated in Scheme 1.

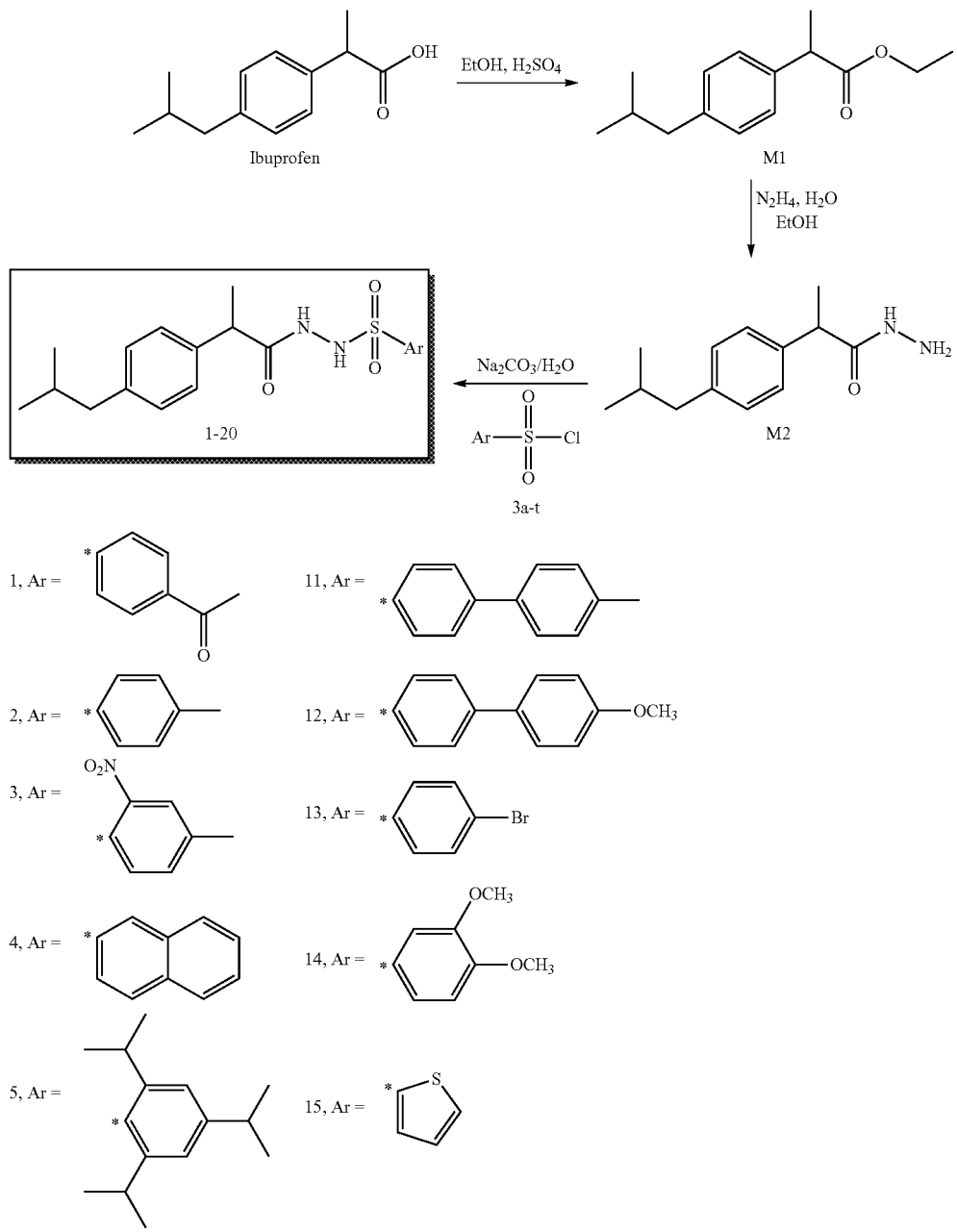

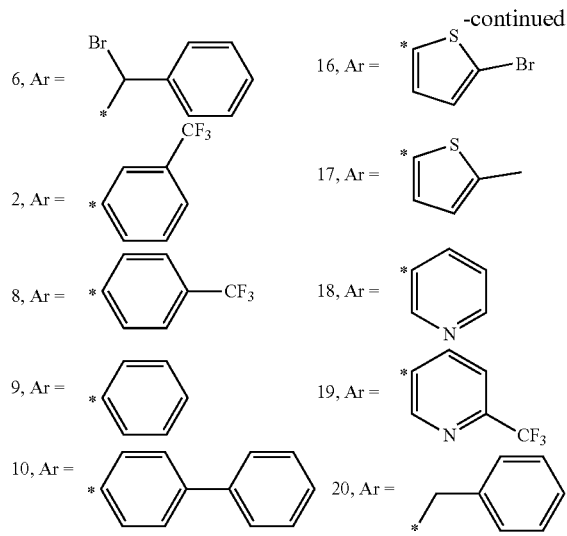

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for cancer. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of diseases such as cancers. Similarly, the present compounds can be used to inhibit FAAH enzyme activity in a patient.

In another embodiment of the present subject matter, the aforementioned compound derivatives demonstrated in vitro anticancer action against human cancer cell lines such as A549 (lung cancer). Accordingly, the present subject matter relates to methods of treating a cancer in a patient by administering one or more of the compounds presented herein to a patient in need thereof. In certain embodiments, the cancer treatable with the present compounds is lung cancer.

Accordingly, in an embodiment of the present subject matter, the sulfonylhydrazide derivatives as described herein engaged for in vitro study towards human cancer cell lines can display an $IC_{50}$ with a nano to micromolar concentration range when exposed to a period of at least 72 hrs. For example, a present compound (10) engaged for in vitro study against A549 (non-small cell lung cancer) cell lines can display an $IC_{50}$ concentration of 0.291 μM at an exposure period of at least 72 hrs. In another example, a present compound (11) engaged for in vitro study against A549 (non-small cell lung cancer) cell lines can display an $IC_{50}$ concentration of 15.970 μM at an exposure period of at least 72 hrs. In a third example, compound 12 engaged for in vitro study against A549 (non-small cell lung cancer) cell lines can display an $IC_{50}$ concentration of 11.710 μM at an exposure period of at least 72 hrs.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

General Procedure to the synthesis of N'-(2-(4-isobutylphenyl) propanoyl) substitute's sulfonohydrazide 1-20

The synthesis of these derivatives was based on the procedure as shown in (Scheme 1). Twenty milliliters of distilled water were added to 0.005 mol of hydrazide derivative M2. The pH was set at 8-10 by using sodium carbonate solution. Then, 0.005 mol of substituted benzene sulfonyl chloride derivative 3a-t were added gradually and the reaction mixture was brought to room temperature and then further stirred for 4-6 hours. The reaction was monitored by thin layer chromatography (TLC) using 7:3 n-hexane/ethyl acetate. After the completion of the reaction, the solid products separated and were filtered, washed and dried.

Example 2

4-acetyl-N'-(2-(4-isobutylphenyl)propanoyl)benzenesulfonohydrazide (1)

The expected product was obtained in accordance with the general procedure for the preparation of N'-(2-(4-isobutylphenyl) propanoyl) substitutes sulfonohydrazide of Example 1 using 4-methoxy(phenyl) as the substituted benzene sulfonyl chloride.

Yield 62% as white solid; m.p. 142-144° C., IR(KBr, cm$^{-1}$) vmax=3301 (NH stretch), 3188 (aromatic C—H stretch), 2956 (aliphatic C—H stretch), 1677 (C=O amide stretch), 1461 (C—N stretch), 1173-1381 (S=O stretch). 1H NMR (500 MHz, DMSO-d6) δ (ppm): 0.80 (d, 6H, J=7 Hz, (CH$_3$)$_2$CH), 1.33-1.35 (d, 3H, 14 J=7 Hz, CH$_3$CH), 1.79 (m, 1H, (CH$_3$)$_2$ CH), 2.13-2.15 (d, 2H, CHCH$_2$), 2.31-2.34 (s, 3H, CH$_3$CO), 3.46-3.48 (q, 1H, J=10 Hz, CH$_3$CH), 7.01-7.03 (d, 2H, J=8 Hz, 3-H, 5-H), 7.20-7.21 (d, 2H, J=7.5 Hz, 2-H, 6-H), 7.53-7.55 (d, 2H, J=8 Hz, 2'-H, 6'-H), 7.67-7.69 (d, 2H, J=9 Hz, 3'-H, 5'-H), 10.23 (s, 1H, CONH), 10.40-10.62 (s, 1H, NHSO$_2$). $^{13}$C NMR (500 MHz, DMSO-d6) δ (ppm): 14.81, 19.3, 22.7, 30.2, 42.8, 44.8, 126.1, 127.5, 127.8, 129.4, 138.9, 139.7, 139.7, 139.9, 172.5, 176.4. HR-MS (m/z) [M+H+] calcd for C$_{21}$H$_{27}$N$_2$O$_4$S, 403.1692; found 403.1632.

Example 3

N'-(2-(4-isobutylphenyl) propanoyl)-4-methylbenzene sulfonohydrazide (2)

The expected product was obtained in accordance with the general procedure for the preparation of N'-(2-(4-isobutylphenyl) propanoyl) substitute's sulfonohydrazide of Example 1 using 4-methyl(phenyl) as the substituted benzene sulfonyl chloride derivative.

Yield 78% as white solid; m.p. 124-126° C., IR(KBr, cm-1) vmax=3340 (NH stretch), 2950 (aromatic C—H stretch), 1675 (C=O amide stretch), 1461 (C—N stretch), 1160-1343 (S=O stretch). 1H NMR (500 MHz, DMSO-d6) δ (ppm): 0.79-0.81 (d, 6H, J=7 Hz, (CH3)2CH), 1.09-1.11 (d, 3H, J=7 Hz, CH3CH), 1.75-1.77 (m, 1H, (CH3)2 CH), 2.30 (s, 3H, phenyl-CH3), 2.36-2.38 (d, 2H, J=7.5 Hz, CHCH2), 3.46-3.47 (q, 1H, J=8 Hz, CH3CH), 7.02-7.03 (d, 4H, J=6.5 Hz, 3-H, 5-H, 2-H, 6-H), 7.12-7.13 (d, 2H, 3J=8 Hz, 3'-H, 5'-H), 7.43-7.45 (d, 2H, J=8 Hz, 2'-H, 6'-H), 9.66 (s, 1H, CONH), 10.20 (s, 1H, NHSO2). 13C NMR (500 MHz, DMSO-d6) δ (ppm): 18.5, 21.3, 22.7, 30.11, 42.8, 44.7, 126.0, 128.2, 128.6, 129.6, 136.2, 138.8, 140.6, 143.5, 172.5. HR-MS (m/z) [M+H+] calcd for C$_{20}$H$_{27}$N$_2$O$_3$S, 375.1742; found 375.1757.

Example 4

N'-(2-(4-isobutylphenyl) propanoyl)-2-nitrobenzene-sulfonohydrazide (3)

The expected product was obtained in accordance with the general procedure for the preparation of N'-(2-(4-isobutylphenyl) propanoyl) substituted sulfonohydrazide of Example 1 using 2-nitro(phenyl) as the substituted benzene sulfonyl chloride derivative.

Yield 64% white solid; m.p. 130-132° C. IR(KBr, cm-1) vmax=3388 (NH stretch), 3145 (aromatic C—H stretch), 1677 (C=O amide stretch), 1552 (NO$_2$ stretch), 1424 (C—N stretch), 1181-1371 (S=O stretch). $^1$H NMR (500 MHz, DMSO-d6) δ (ppm): 0.79-0.81 (d, 6H, J=7 Hz, (CH$_3$)$_2$CH), 1.15-1.17 (d, 3H, J=7 Hz, (CH$_3$CH)), 1.75 (n 1H, (CH$_3$)$_2$ CH)), 2.35-2.46 (d, 2H, J=7.5 Hz, CHCH$_2$), 3.49 (q, 1H, CH$_3$CH), 7.04-7.06 (d, 4H, J=14 Hz, 2-H, 3-H, 5-H, 6-H), 7.60-7.64 (m, 1H, 5'-H), 7.74-7.78 (m, 1H, 4'-H), 7.79-7.81 (d, 1H, J=7.5 Hz, 6'-H), 7.90-7.92 (d, 1H, J=8 Hz, 3'-H), 10.02 (s, 1H, CONH), 10.41 (s, 1H, NHSO2). 13C NMR (500 MHz, DMSO-d6) δ (ppm): 18.3, 22.7, 30.1, 42.8, 44.7, 1249, 127.5, 129.3, 129.6, 131.4, 132.7, 135.1, 138.6, 140.1, 1484, 173.1, HR-MS (mi/z) [M+H+] calcd for C$_{19}$H$_{24}$N$_3$O$_5$S, 406.1437; found 406.1480.

Example 5

N'-(2-(4-isobutylphenyl)propanoyl)naphthalene-2-sulfonohydrazide (4)

The expected product was obtained in accordance with the general procedure for the preparation of N'-(2-(4-isobutylphenyl) propanoyl) substituted sulfonohydrazide of Example 1 using naphthalene as the substituted benzene sulfonyl chloride derivative.

Yield 83% as white solid; m.p. 149-151° C., IR(KBr, cm-1) vmax=3329 (NH stretch), 2950 (aromatic C—H stretch), 1691 (C=O amide stretch), 1410 (C—N stretch), 1171-1334 (S=O stretch). 1H NMR (500 MHz, DMSO-d6) δ (ppm): 078-0.80 (d, 6H, J=8 Hz, (CH$_3$)$_2$CH), 1.01-1.03 (d, 3H, 33=7.5 Hz, CH$_3$CH), 1.74 (m, 1H, (CH$_3$)$_2$ CH), 2.45-2.46 (d, 2H, J=6.5 Hz, CHCH$_2$), 3.41-3.44 (q, 1H, J=7 Hz, CH$_3$CH), 6.85 (d, 4H, J=6.5 Hz, 2-H, 3-H, 5-H, 6-H), 7.60-7.68 (2H, m, 6-H, 7-H), 7.93 (1H, d, 3J=8.5 Hz, 5'-H), 7.96 (d, 1H, J=9 Hz, 8'-H), 7.98 (d, 1H, t=9 Hz, 4'-4), 8.01 (d, 1H, J=8 Hz, 3'-H), 8.25 (s, 1H, 1'-H), 9.91 (s, 1H, CONH), 10.26 (s, 1H, NHSO$_2$). $^{13}$C NMR (500 MHz, DMSO-d6) δ (ppm): 18.5, 22.7, 30.1, 42.7, 44.7, 123.8, 127.3, 127.8, 128.3, 129.2, 129.2, 129.8, 132.0, 135.0, 136.5, 138.6, 139.8, 172.6. HR-MS (m/z) [M+H+] calcd for C$_{23}$H$_{27}$N$_2$O$_3$S, 411.1742; found 411.1735.

Example 6

N'-(2-(4-isobutylphenyl) propanoyl)-2, 4, 6 triisopropyl benzene sulfonohydrazide (5)

The expected product was obtained in accordance with the general procedure for the preparation of N'-(2-(4-isobutylphenyl) propanoyl substituted sulfonohydrazide of Example 1 using 1, 3, 5-tri-isopropyl(phenyl) as the substituted benzene sulfonyl chloride derivative.

Yield 81% as white solid; m.p. 175-177° C., IR(KBr, cm-1) vmax=3323 (NH stretch), 2960 (aromatic C—H stretch), 1688 (C=O amide stretch), 1368 (C—N stretch), 1152-1329 (S=O stretch). 1H NMR (500 MHz, DMSO-d6) δ (ppm): 0.80 (d, 6H, J=6.5 Hz, (CH$_3$)$_2$CH), 1.12 (d, 3H, J=7 Hz, CH$_3$CH), 1.16 (d, 18H, J=7 Hz, phenyl (3)×CH (CH$_3$)$_2$), 1.73 (m, 1H, (CH$_3$)$_2$ CH), 2.34 (d, 2H, J=7 Hz, CHCH$_2$), 2.86 (m, 3H, phenyl (3)×CH(CH3)2), 3.96 (q, 1H, J=7 Hz, CH3CH), 6.96-6.98 (d, 2H, J=8 Hz, 3-H, 5-H), 7.06-7.08 (d, 2H, J=8 Hz, 2-H, 6-H), 7.13 (s, 2H, 3'-H, 5'-H), 9.38 (s, 1H, CONH), 10.08 (s, 1H, NHSO$_2$). $^{13}$C NMR (500 MHz, DMSO-d6) δ (ppm): 19.3, 22.7, 24.0, 25.2, 29.9, 33.9, 42.9, 44.8, 123.8, 127.5, 129.2, 133.1, 138.9, 139.9, 151.2, 152.7, 173.3. HR-MS (m/z) [M+H+] calcd for C$_{28}$H$_{43}$N$_2$O$_3$S, 487.2994; found 487.3075.

Example 7

1-Bromo-N'-(2-(4-isobutylphenyl) propanoyl)-1-phenylmethane sulfonohydrazide (6)

The expected product was obtained in accordance with the general procedure for the preparation of N'-(2-(4-isobutylphenyl) propanoyl) substitute's sulfonohydrazide of Example 1 using ethyl-2-bromo-phenyl as the substituted benzene sulfonyl chloride derivative.

Yield 81% as white solid; m.p. 158-160° C., IR(KBr, cm-1) vmax=3339 (NH stretch), 2953 (aromatic C—H stretch), 1678 (C=O amide stretch), 1541 (C—N stretch), 1163-1346 (S=O stretch). $^1$H NMR (500 MHz, DMSO-d6) δ (ppm): 0.85 (d, 6H, J=7 Hz, (CH3)2CH), 1.14-1.15 (d, 3H, J=7 HZ, CH$_3$CH), 1.76-1.78 (m, 1H, (CH$_3$)$_2$ CH), 2.40-2.42 (d, 2H, J=8.5 Hz, CHCH$_2$), 3.45-3.46 (q, 1H, J=7 Hz, CH$_3$CH), 6.96-6.98 (s, 1H, SO$_2$CHBr), 7.01 (d, 2H, J=8 Hz, 3-H, 5-H), 7.04 d, 2H, J=6.5 Hz, 2-H, 6-H), 7.45-7.47 (m, 3H, 3'-H, 4'-H, 5'-H), 7.53-7.55 (d, 2H, J=11 Hz, 2'-H, 6'-H), 9.94 (s, 1H, CONH), 10.29 (s, 1H, NHSO$_2$). $^{13}$C NMR (500 MHz, DMSO-d6) δ (ppm): 18.5, 227, 30.2, 42.9, 44.7, 58.1, 127.5, 128.6, 128.8, 129.4, 129.8, 131.4, 138.9, 140.2, 173.9. HR-MS (m/z) [M+H+] calcd for C$_{20}$H$_{26}$BrN$_2$O$_3$S, 453.0848; found 453.0847.

Example 8

N'-(2-(4-isobutylphenyl) propanoyl)-3-(trifluoromethyl) benzene sulfonohydrazide (7)

The expected product was obtained in accordance with the general procedure for the preparation of N'-(2-(4-isobutylphenyl) propanoyl) substitute's sulfonohydrazide of Example 1 using 3-triflouromethyl(phenyl) as the substituted benzene sulfonyl chloride derivative.

Yield 86% white solid; m.p. 148-150° C. IR(KBr, cm-1) vmax=3330 (NH stretch), 2949 (aromatic C—H stretch), 1669 (C=O amide stretch), 1464 (C—N stretch), 1127 (C—F stretch), 1166-1331 (S=O stretch). $^1$H NMR (500 MHz, DMSO-d6) δ (ppm): 0.82-0.83 (d, 6H, J=6.5 Hz, CH$_3$)$_2$CH) 1.12 d, 3H, J=7 Hz, CH$_3$CH), 1.75-1.76 (m, 1H, (CH$_3$)$_2$ CH), 2.34-2.36 (d, 2H, J=7.5 Hz, CHCH$_2$), 3.45-3.47 (q, 1H, 3J=7 Hz, CH$_3$CH), 6.98-7.03 (d, 4H, J=11 Hz, 3-H, 5-H, 2-H, 6-H), 7.61-7.64 (m, 1H, 5'-H), 7.82-7.84 (d, 1H, J=8.5 Hz, 4'-H), 7.93 (s, 1H, 2'-1), 7.95-7.97 (d, 1H, J=8 Hz, 6'-H), 10.17 (s, 1H, CONH), 10.32 (s, 1H, NHSO$_2$). $^{13}$C NMR (500 MHz, DMSO-d6) δ (ppm): 18.4, 22.6, 30.1, 42.8, 44.7, 124.6, 127.4, 129.2, 130.1, 130.8, 132.2, 138.5, 138.6, 140.0, 40.8, 172.8. HR-MS (m/z) [M+H+] calcd for C$_{20}$H$_{24}$F$_3$N$_2$O$_3$S, 429.1460; found 429.1470.

Example 9

N'-(2-(4-isobutylphenyl) propanoyl)-4-(trifluoromethyl) benzene sulfonohydrazide (8)

The expected product was obtained in accordance with the general procedure for the preparation of N'-(2-(4-isobutylphenyl) propanoyl) substitute's sulfonohydrazide of Example 1 using 4-triflouromethyl(phenyl) as the substituted benzene sulfonyl chloride derivative.

Yield 82% as white solid; m.p. 146-148° C. IR(KBr, cm-1) vmax=3346 (NH stretch), 2957 (aromatic C—H stretch), 1674 (C=O amide stretch), 1462 (C—N stretch), 1134 (C—F stretch), 1168-1350 (S=O stretch). 1H NMR (500 MHz, DMSO-d6) δ (ppm): 0.83-0.85 (d, 6H, J 9 Hz, (CH$_3$)$_2$CH), 1.12 (d, 3H, J=8 Hz, CH$_3$CH), 1.76 (m, 1H, (CH$_3$)$_2$ CH), 2.36-2.46 (d, 2H, J=14.5 Hz, CHCH$_2$), 3.45-3.47 (q, 1H, J=7.5 Hz, CH$_3$CH), 6.96-6.98 (d, 4H, J=8 Hz, 2-H, 3-H, 5-H, 6-H), 7.69-7.71 (d, 2H, J=8.5 Hz, 2-H, 6'-H), 7.74-7.76 (d, 2H, J=9 Hz, 3'-H, 5'-H), 10.15 (s, 1H, CONH), 10.33 (s, 1H, NHSO2). 13C NMR (500 MHz, DMSO-d6) δ (ppm): 18.3, 22.7, 30.1, 42.8, 44.7, 126.2, 127.3, 127.5, 129.1, 129.23, 133.10, 138.6, 140.1, 143.1, 172.7, HR-MS (m/z) [M+H+] calcd for C$_{20}$H$_{24}$F$_3$N$_2$O$_3$S, 429.1460; found 429.1487.

Example 10

N'-(2-(4-isobutylphenyl) propanoyl) benzenesulfonohydrazide (9)

The expected product was obtained in accordance with the general procedure for the preparation of N'-(2-(4-isobutylphenyl) propanoyl) substitute's sulfonohydrazide of Example 1 using phenyl as the substituted benzene sulfonyl chloride derivative.

Yield 73% as white solid; m.p. 116-118° C., IR(KBr, cm-1) vmax=3335 (NH stretch), 3040 (aromatic C—H stretch), 1678 (C=O amide stretch), 1447 (C—N stretch), 1161-1341 (S=O stretch), 1H NMR (500 MHz, DMSO-d6) δ (ppm): 0.82 (d, 6H, J=8 Hz, (CH$_3$)$_2$CH)), 1.13 (d, 3H, J=7.5 Hz, CH$_3$CH), 1.79 (m, 1H, (CH$_3$)$_2$CH)), 2.36 (d, 2H, J=7 Hz, 2-H, 3-H, 5-H, 6-H), 7.14-7.15 (m, 1H, 4'-H), 7.34-7.42 (m, 2H, 3'-H, 5'-H), 7.53-7.58 (m, 2H, 2'-H, 6'-H), 9.81 (s, 1H, CONH), 10.23 (s, 1H, NHSO$_2$). 13C NMR (500 MHz, DMSO-d6) δ (ppm): 18.4, 22.7, 30.2, 42.8, 44.8, 127.5, 128.1, 129.2, 129.4, 129.6, 133.3, 138.8, 140.0, 172.5. HR-MS (m/z) [M+H+] calcd for C$_{19}$H$_{25}$N$_2$O$_3$S, 361.1586; found 361.1595.

Example 11

N'-(2-(4-isobutylphenyl) propanoyl)-[1, 1'-biphenyl]-4-sulfonohydrazide (10)

The expected product was obtained in accordance with the general procedure for the preparation of N'-(2-(4-isobutylphenyl) propanoyl) substitute's sulfonohydrazide of Example 1 using 4-phenyl-phenyl as the substituted benzene sulfonyl chloride derivative.

Yield 96% as white solid; m.p. 156-158° C., IR(KBr, cm-1) vmax=3332 (NH stretch), 3036 (aromatic C—H stretch), 1677 (C=O amide stretch), 1460 (C—N stretch), 1161-1341 (S=O stretch), 1H NMR (500 MHz, DMSO-d6) δ (ppm): 0.81-0.82 (d, 6H, J=6.5 Hz, (CH$_3$)$_2$CH), 1.15 (d, 3H, J=7 Hz, CH$_3$CH), 1.72 (m, 1H, J=6.5 Hz, (CH$_3$)$_2$ CH)), 2.45-2.46 (d, 2H, J=6.5 Hz, CHCH$_2$), 3.48-3.49 (q, 1H, J=7.5 Hz, CH$_3$CH)), 6.99-7.00 (d, 4H, J 6 Hz, 2-H, 3-H, 5-H, 6-H), 7.41-7.42 (m, 1H, 4b-H), 7.47-7.50 (m, 2H, 3b-1H, 5b-H), 7.65-7.66 (d, 6H, J=8.5 Hz, 2a-H, 3a-H, 5a-H, 6a-H, 2b-H, 6b-H), 9.81 (s, 1H, CONH), 10.27 (s, 1H, NHSO$_2$). $^{13}$C NM R (500 MHz, DMSO-d6) δ (ppm): 18.4, 22.7, 30.1, 42.77, 44.7, 127.3, 127.5, 128.8, 129.1, 129.2, 129.7, 139.0, 139.9, 144.6, 172.6. HR-MS (m/z) [M+H+] calcd for C$_{25}$H$_{29}$N$_2$O$_3$S, 437.1899; found 437.1933.

Example 12

N'-(2-(4-isobutylphenyl) propanoyl)-4'-methyl-[1, 1'-biphenyl]-4-sulfonohydrazide (11)

The expected product was obtained in accordance with the general procedure for the preparation of N'-(2-(4-isobutylphenyl) propanoyl) substituted sulfonohydrazide of Example 1 using 4-phenyl-8-methyl-phenyl as the substituted benzene sulfonyl chloride derivative.

Yield 94% as white solid; m.p. 160-162° C., IR(KBr, cm$^{-1}$) vmax=3345 (NH stretch), 3037 (aromatic C—H stretch), 1676 (C=O amide stretch), 1458 (C—N stretch), 1162-1341 (S=O stretch). $^1$H NMR (500 MHz, DMSO-d6) δ (ppm): 0.82 (d, 6H, J=6.5 Hz, (CH$_3$)$_2$CH), 1.14 (d, 3H, J=7.5 Hz, CH$_3$CH), 1.73 (m, 1H, (CH$_3$)$_2$ CH), 2.30-2.33 (s 3H, bi-phenyl-CH$_3$), 2.46 (d, 2H, J=5 Hz, CHCH$_2$), 3.47-3.48 (q, 1H, J=7 Hz, CH$_3$CH), 6.96-6.98 (d, 4H, J=8 Hz, 3-H, 5-H, 2-H, 6-H), 7.29-7.28 (d, 2H, J=8 Hz, 3b-H, 5b-H), 7.54-7.56 (d, 2H, J=8 Hz, 2b-H, 6b-H), 7.62 (d, 4H, J=8 Hz, 2a-H, 3a-H, 5a-H, 6a-H), 9.80 (s, 1H, CONH), 10.25 (s, 1H, NHSO2). 13C NMR (500 MHz, DMSO-d6) δ (ppm): 18.4, 21.2, 22.7, 30.1, 42.8, 44.7, 126.9, 127.3, 127.5, 128.8, 129.2, 130.3, 136.1, 137.5, 138.6, 138.7, 139.9, 144.6, 172.5. HR-MS (m/z) [M+H+] calcd for C$_{26}$H$_{31}$N$_2$O$_3$S, 451.2055; found 451.2070.

Example 13

N'-(2-(4-isobutylphenyl) propanoyl)-4'-methoxy-[1, 1'-biphenyl]-4sulfonohydrazide (12)

The expected product was obtained in accordance with the general procedure for the preparation of N'-(2-(4-isobutylphenyl) propanoyl) substitute's sulfonohydrazide of Example 1 using 4-phenyl-8-methoxy-phenyl as the substituted benzene sulfonyl chloride derivative.

Yield 77% as white solid; m.p. 167-169° C., IR(KBr, cm-1) vmax=3350 (NH stretch), 3224 (aromatic C—H stretch), 2953 (OCH$_3$ stretch), 1690 (C=O amide stretch), 1490 (C—N stretch), 1166-1327 (S=stretch). 1H NMR (500 MHz, DMSO-d6) δ (ppm): 0.80 (d, 6H, J=8 Hz, (CH$_3$)$_2$CH), 1.11-1.13 (d, 3H, J=6.5 Hz, CH$_3$CH), 1.70-1.75 (m, 1H, (CH$_3$) CH), 2.32-233 (d, 2H, J=7 Hz, CHCH$_2$), 3.49-3.50 (q, 1H, J=7 Hz, CH$_3$CH), 3.77 (s, 3H, Biphenyl-OCH$_3$), 7.01-7.02 (d, 4H, J=8.5 Hz, 3-H, 5-H, 2-H, 6-H), 7.04 (d, 2H, J=8.5 Hz, 3b-H, 5b-H), 7.61-7.62 (d, 6H, J=9 Hz, 2a-H, 3a-H, 5a-H, 6a-H, 2b-H, 6b-H), 9.78 (s, 1H, CONH), 10.27 (s, 1H, NHSO$_2$). $^{13}$C NMR (500 MHz, DMSO-d6) δ (ppm): 18.4, 22.7, 30.1, 418, 44.7, 55.8, 114.8, 126.5, 127.5, 128.7, 128.8, 129.2, 131.2, 137.0, 138.7, 139.9, 144.4, 160.3, 172.5. HR-MS (m/z) [M+H+] calcd for C$_{26}$H$_{31}$N$_2$O$_4$S, 467.2005; found 467.2072.

Example 14

4-Bromo-N'-(2-(4-isobutylphenyl)propanoyl)benzenesulfonohydrazide (13)

The expected product was obtained in accordance with the general procedure for the preparation of N'-(2-(4-isobutylphenyl) propanoyl) substitute's sulfonohydrazide of Example 1 using 4-bromo-phenyl as the substituted benzene sulfonyl chloride derivative.

Yield 86% as white solid; m.p. 153-155° C., IR(KBr, cm-1) vmax=3329 (NH stretch), 2952 (aromatic C—H stretch), 1676 (C=O amide stretch), 1465 (C—N stretch), 1162-1343 (S=O stretch). 1H NMR (500 MHz, DMSO-d6) δ (ppm): 0.81-0.82 (d, 6H, J=8 Hz, (CH$_3$)$_2$CH), 1.11-1.12 (d, 3H, J=7 Hz, CH$_3$CH), 1.76-1.77 (m, 1H, (CH$_3$)$_2$ CH), 2.35 (d, 2H, J=6.5 Hz, CHCH$_2$), 3.44 (q, 1l, J=7.5 Hz, CH$_3$CH), 6.95-6.96 (d, 2H, J=8 Hz, 3-H, 5-H), 7.02-7.04 (d, 2H, J=7 Hz, 2'-H, 6-H), 7.44-7.46 (d. 2H, J=8.5 Hz, 2'-H, 6'-H), 7.53-7.55 (d, 2H, J=9 Hz, 3'-H, 5'-H), 9.92 (s, 1H, CONH), 10.27 (s, 1H, NHSO$_2$). $^{13}$C NMR (500 MHz, DMSO-d6) δ (ppm): 18.3, 22.7, 30.2, 42.8, 44.8, 127.3, 127.5, 129.2, 130.1, 132.2, 138.3, 138.6, 140.1, 172.6. HR-MS (n/z) [M+H+] calcd for C$_{19}$H$_{24}$BrN$_2$O$_3$S, 439.0691; found 439.3075.

Example 15

N'-(2-(4-isobutylphenyl) propanoyl)-3, 4-dimethoxybenzene sulfonohydrazide (14)

The expected product is obtained in accordance with the general procedure for the preparation of N'-(2-(4-isobutylphenyl) propanoyl) substitute's sulfonohydrazide of Example 1 3,4-dimethoxy(phenyl) as the substituted benzene sulfonyl chloride derivative.

Yield 62% as white solid; m.p. 161-163° C., IR(KBr, cm-1) vmax=353 (NH stretch), 3186 (aromatic C—H stretch), 2955 (O—CH3 stretch), 1664 (C=O amide stretch), 1160-1338 (S=O stretch), 1H NMR (500 MHz, DMSO-d6) δ (ppm): 0.81 (d. 6H, J=6.5 Hz, (CH₃)₂CH), 1.12 (d, 3H, J=7 Hz, CH₃CH), 1.75 (m, 1H, J=6 Hz, (CH₃)₂ CH), 2.34-2.36 (d, 2H, J=7.5 Hz, CHCH₂), 3.44-3.45 (q, 1H, J=7 Hz, CH₃CH), 3.68 (s, 3H, phenyl-(4')OCH₃), 3.77 (s, 3H, phenyl-(3')OCH₃), 6.86-6.88 (d, 1H, J=8.5 Hz, 5'-H), 6.98 (d, 4H, J=7 Hz, 2-H, 3-H, 5-H, 6-H), 7.14-7.16 (d, 1H, J=8 Hz, 6-H), 7.17 (s, 1H, 2-H), 9.59 (s, 1H, CONH), 10.12 (s, 1H, NHSO₂). ¹³C NMR (500 MHz, DMSO-d6) δ (ppm): 18.6, 22.7, 301, 42.8, 44.7, 56.3, 111.0, 111.1, 122.3, 127.5, 129.2, 130.5, 138.8, 139.9, 148.8, 152.9, 172.5. HR-MS (m/z) [M+H+] calcd for C₂₁H₂₉N₂O₅S, 421.1797; found 421.1796.

Example 16

N'-(2-(4-isobutylphenyl)propanoyl)thiophene-2-sulfonohydrazide (15)

The expected product is obtained in accordance with the general procedure for the preparation of N'-(2-(4-isobutylphenyl) propanoyl) substitute's sulfonohydrazide of Example 1 thiophene as the substituted benzene sulfonyl chloride derivative.

Yield 93% as pale yellow solid; m.p. 86-88° C., IR(KBr, cm-1) vmax=3313 (NH stretch), 2868 (aromatic C—H stretch), 1678 (C=O amide stretch), 1461 (C—N stretch), 1158-1345 (S=O stretch), 1H NMR (500 MHz, DMSO-d6) δ (ppm): 081-0.83 (d, 6H, J=8 Hz, (CH₃)₂CH), 1.16-1.18 (d, 3H, J=8 Hz, CH₃CH), 1.74-1.78 (m, 1H, (CH₃)₂ CH), 2.34-2.35 (d, 2H, J=7.5 Hz, CHCH₂), 3.47-3.48 (q, 1H, J=7.5 Hz, CH₃CH), 6.97-6.98 (m, 1H, 4'-H), 7.01-7.02 (d, 4H, J=8 Hz, 3-H, 5-H, 2-H, 6-H), 7.24-7.25 (d. 1H, J=5 Hz, 3'-H), 7.85 (d, 1H, J=8 Hz, 5'-H), 9.91 (s, 1H, CONH), 10.31 (s, 1H, NHSO₂). ¹³C NMR (500 MHz, DMSO-d6) δ (ppm): 18.5, 22.7, 30.2, 42.9, 44.8, 127.6, 127.9, 129.3, 129.5, 133.8, 134.4, 138.8, 140.0, 172.7. HR-MS (m/z) [M+H+] calcd for C₁₇H₂₃N₂O₃S₂, 367.115; found 367.1174.

Example 17

5-Bromo-N'-(2-(4-isobutylphenyl) propanoyl) thiophene-2-sulfonohydrazide (16)

The expected product is obtained in accordance with the general procedure for the preparation of N'-(2-(4-isobutylphenyl) propanoyl) substitute's sulfonohydrazide of Example 1 using 5-bromo-thiophene as the substituted benzene sulfonyl chloride derivative.

Yield 66% as pale yellow solid; m.p. 149-151° C., IR(KBr, cm-1) vmax=3317 (NH stretch), 2951 (aromatic C—H stretch), 1676 (C=O amide stretch), 1458 (C—N stretch), 1156-1345 (S=O stretch). 1H NMR (500 MHz, DMSO-d6) δ (ppm): 0.80-0.82 (d, 6H, J=6.5 Hz, (CH3)2CH), 1.17 (d, 3H, J=8 Hz, CH3CH), 1.75-1.78 (m, 1H, (CH3)2 CH), 2.35 (d, 2H, J=7.5 Hz, CHCH2), 3.50 (q, 1H, J=7 Hz, CH3CH), 7.01-7.03 (d, 4H, J=7 Hz, 3-H, 5-H, 2-H, 6-H), 7.07-7.09 (d, 1H, J=6 Hz, 3'-H), 7.12-7.14 (d, 1H, J=8 Hz, 4'-H), 10.13 (s, 1H, CONH), 10.34 (s, 1H, NHSO2). ¹³C NMR (500 MHz, DMSO-d6) δ (ppm): 18.6, 22.7, 30.2, 42.9, 44.7, 120.1, 127.6, 129.3, 129.6, 131.6, 134.1, 138.7, 140.1, 172.84. HR-MS (m/z) [M+H+] calcd for C17H22BrN2O3S2, 445.0255; found 445.9917.

Example 18

N'-(2-(4-isobutylphenyl)propanoyl)-5-methylthiophene-2-sulfonohydrazide (17)

The expected product is obtained in accordance with the general procedure for the preparation of N'-(2-(4-isobutylphenyl) propanoyl) substitute's sulfonohydrazide of Example 1 using 5-methylthiophene as the substituted benzene sulfonyl chloride derivative.

Yield 57% as white solid; m.p. 127-129° C. IR(KBr, cm-1) vmax=3341 (NH stretch), 2950 (aromatic C—H stretch), 1677 (C=O amide stretch), 1440 (C—N stretch), 1154-1346 (S=O stretch). 1H NMR (500 MHz, DMSO-d6) δ (ppm): 0.80-0.81 (d, 6H, J=5.5 Hz, (CH₃)₂CH), 1.15-1.16 (d, 3H, J=7.5 Hz, CH₃CH), 1.75-1.78 (m, 1H, (CH₃)₂ CH), 2.34 (d, 2H, J=6 Hz, CHCH₂), 2.41 (s, 3H, thiophene-CH₃), 3.50 (q, 1H, J=7 Hz, CH₃CH), 6.69-6.70 (d, 1H, J=6 Hz, 4'-H), 7.01-7.03 (d, 1H, J=8.5 Hz, 3'-H), 7.06-7.08 (d, 4H, J=8 Hz, 3-H, 5-H, 2-H, 6-H), 9.79 (s, 1H, CONH), 10.24 (s, 1H, NHSO₂). ¹³C NMR (500 MHz, DMSO-d6) δ (ppm): 15.7, 18.5, 22.7, 30.2, 42.9, 44.8, 126.7, 127.6, 128.9, 133.9, 135.9, 138.84, 140.0, 148.4, 172.6. HR-MS (m/z) [M+H+] calcd for C₁₈H₂₅N₂O₃S₂, 381.1307; found 381.1298.

Example 19

N'-(2-(4-isobutylphenyl)propanoyl)pyridine-3-sulfonohydrazide (18)

The expected product is obtained in accordance with the general procedure for the preparation of N'-(2-(4-isobutylphenyl) propanoyl) substitute's sulfonohydrazide of Example 1 pyridine as the substituted benzene sulfonyl chloride derivative.

Yield 32% as pale yellow solid; m.p. 95-97° C. IR(KBr, cm-1) vmax=3319 (NH stretch), 2955 (aromatic C—H stretch), 1676 (C=O amide stretch), 1462 (C—N stretch), 1168-1344 (S=O stretch). 1H NMR (500 MHz, DMSO-d6) δ (ppm): 0.80-0.81 (d, 6H, J=6.5 Hz, (CH₃)₂CH), 1.11 (d, 3H, J=7.5 Hz, CH₃CH), 1.75-1.76 (m, 1H, (CH₃)₂ CH), 2.35 (d, 2H, J=6.5 Hz, CHCH₂), 3.45 (q, 1H, J=7 Hz, CH₃CH), 6.97-6.98 (d, 4H, J=6.5 Hz, 2-H, 6-H, 3-H, 5-H), 7.41 (m, 1H, 5'-H), 7.18 (d, 1H, J=8.5 Hz, 6'-H), 7.85-7.87 (d, 1H, J=6.5 Hz, 4'-H), 8.71 (s, 1H, 2'-H), 8.74 (s, ¹H, CONH), 10.33 (s, 1H, NHSO₂). ¹³C NMR (500 MHz, DMSO-d6) δ (ppm): 18.3, 22.7, 30.2, 42.8, 44.7, 124.2, 127.3, 127.5, 129.3, 136.0, 138.6, 140.1, 148.4, 153.7, 172.8. HR-MS (m/z) [M+H+] calcd for C₁₈H₂₄N₃O₃S, 362.1538; found 362.9930.

Example 20

N'-(2-(4-isobutylphenyl)propanoyl)-6-(trifluoromethyl)pyridine-3sulfonohydrazide The expected product is obtained in accordance with the general procedure for the preparation of N'-(2-(4-isobutylphenyl) propanoyl) substitute's sulfonohydrazide of Example 1 using 6-(trifluoromethyl)pyridine as the substituted benzene sulfonyl chloride derivative.

Yield 82% as white solid; m.p. 165-167° C. IR(KBr, cm-1) vmax=3346 (NH stretch), 2958 (aromatic C—H stretch), 1672 (C=O amide stretch), 1462 (C—N stretch), 1169-1334 (S=O stretch). ¹H NMR (500 MHz, DMSO-d6) δ (ppm): 0.79 (d, 6H, J=7 Hz, (CH₃)₂CH), 1.09-1.11 (d, 3H, J=8 Hz, CH₃CH), 1.72-1.75 (m, 1H, (CH₃)₂ CH), 2.35 (d, 2H, J=7 Hz, CHCH₂), 3.44-3.45 (q, 1H, J=7 Hz, CH₃CH), 6.95-6.97 (d, 4H, J=8 Hz, 2-H, 6-H, 3-H, 5-H), 7.82 (d, 1H, J=6.5 Hz, 5'-H), 7.85 (d, 1H, J=8.5 Hz, 4'-H), 8.16 (s, 1H, 2'-H), 8.87 (s, 1H, CONH), 10.44 (s, 1H, NHSO₂). ¹³C NMR (500 MHz, DMSO-d6) δ (ppm): 18.2, 22.6, 30.1, 42.7, 44.7, 120.9, 121.3, 127.3, 129.3, 135.8, 138.6, 139.0, 140.1, 147.7, 149.0, 173.1. HR-MS (m/z) [M+H+] calcd for $C_{19}H_{23}F_3N_3O_3S$, 430.1412; found 430.1411.

Example 21

N'-(2-(4-isobutylphenyl)propanoyl)-1-phenylmethanesulfonohydrazide (20)

The expected product is obtained in accordance with the general procedure for the preparation of N'-(2-(4-isobutylphenyl) propanoyl) substitute's sulfonohydrazide of Example 1 using 1-phenyl methane as the substituted benzene sulfonyl chloride derivative.

Yield 58% as white solid; m.p. 143-145° C. IR(KBr, cm-1) vmax=3329 (NH stretch), 2953 (aromatic C—H stretch), 1679 (C=O amide stretch), 1544 (C—N stretch), 1143-1335 (S=O stretch). $^1$H NMR (500 MHz, DMSO-d6) δ (ppm): 0.81-0.83 (d, 6H, J=8.5 Hz, $(CH_3)_2CH$), 1.34-1.35 (d, 3H, J=6.5 Hz, $CH_3CH$), 1.75-1.78 (m, 1H, $(CH_3)_2$ CH), 2.38-2.40 (d, 2H, J=8 Hz, $CHCH_2$), 3.64 (q, 1H, J=7 Hz, $CH_3CH$), 4.03-4.05 (d, 1H, J=14 Hz, SO2-CH-phenyl), 4.16-4.18 (d, 1H, J=13.5 Hz, $SO_2$—CH-phenyl), 7.07-7.08 (d, 2H, J=8 Hz, 3-H, 5-H), 7.24-7.25 (d, 2H, J=8 Hz, 2-H, 6-H), 7.26-7.29 (m, 5H, 2'-H, 3'-H, 4'-H, 5'-H, 6'-H), 9.49 (s, 1H, CONH), 10.34 (s, 1H, $NHSO_2$). $^{13}$C NMR (500 MHz, DMSO-d6) δ (ppm): 18.4, 22.7, 22.7, 30.2, 42.8, 44.8, 127.6, 128.3, 129.2, 129.6, 130.1, 132.2, 138.5, 140.1, 172.6. HR-MS (m/z) [M+H+] calcd for $C_{20}H_{27}N_2O_3S$, 375.1742; found 375.1743.

Pharmacological Activity

Example 22

Inhibition of FAAH Activity

Assay was performed using kits (#10005196) purchased from Cayman Chemicals (Anne Arbor, MI, USA). Ibuprofen was acquired as a generous gift from Tabuk Pharmaceuticals (Tabuk, SA). Doxorubicin was purchased from Sigma (St. Luis, MI, USA). Assay was performed using the FAAH inhibitor screening assay kit from Cayman Chemicals according to the manufacturer's protocol. Release of the fluorescent product, 7-amino-4-methylcoumarin (AMC), from the hydrolysis of AMC-arachidonoyl amide, mediated by FAAH at 37° C., was recorded using a plate reader with an excitation filter of 340-360 nm and an emission filter of 450-465 nm. Inhibitors were preincubated for 30 min at indicated concentrations with the enzyme prior to the addition of substrate to initiate the reaction. Change in fluorescence with time was taken as enzyme activity and the extent of inhibition was calculated from the initial rates. Final DMSO concentration was kept at 2% (v/v) in the assay. Each concentration was repeated three times (Triplicate) to conform to statistical accuracy. Percentage of inhibition at 10 µM was measured for all compounds. Compounds which were able to inhibit the enzyme activity more than 50% at 10 µM were considered eligible for $IC_{50}$ calculations. For $IC_{50}$, the inhibition assay was performed at 1.0, 0.1, 0.01, 0.001 and 0.0001 µM concentration of compound under assay. The hFAAH inhibition was calculated as compared to activity observed with vehicle. $IC_{50}$ values were calculated using Prism v.7.02 for each column separately (singlet concentration). The compound's $IC_{50}$ was calculated using InStat v.3 software (GraphPad Software, San Diego, CA) which was also used for calculation of standard error of means (SEM). Referring to FIG. 1, inhibition of hFAAH by compound 10 is shown.

By way of example, Table 1 shows inhibition of hFAAH and A549 NSCLC cell lines by compounds 1-20. $IC_{50}$ is the concentration at which 50% of the cells were inhibited after treatment with a target compound. SEM is the standard error of means.

| Compound | hFAAH Inhibition | | | | A549 Cell Line Inhibition | |
|---|---|---|---|---|---|---|
| | % Inhibition at 10 µM | SEM | $IC_{50}$ (µM) | SEM | $IC_{50}$ (µM) | SEM |
| 1 | 33.61 | 1.63 | | | >100 | 0.947 |
| 2 | 63.49 | 1.50 | 1.461 | 0.175 | >100 | |
| 3 | 45.51 | 5.59 | | | 55.623 | 0.693 |
| 4 | 87.77 | 1.06 | 0.179 | 0.038 | 52.960 | 5.12 |
| 5 | 8.85 | 5.69 | | | 72.960 | 2.917 |
| 6 | 20.59 | 1.00 | | | >100 | |
| 7 | 36.15 | 1.82 | | | >100 | |
| 8 | 73.97 | 4.33 | 1.198 | 0.092 | 40.106 | 3.536 |
| 9 | 99.93 | 1.84 | 0.144 | 0.038 | 46.390 | 1.935 |
| 10 | 98.11 | 0.61 | 0.0056 | 0.0009 | 0.291 | 0.016 |
| 11 | 95.32 | 2.29 | 0.072 | 0.003 | 15.970 | 1.266 |
| 12 | 99.00 | 4.78 | 0.141 | 0.029 | 11.710 | 1.702 |
| 13 | 48.73 | 1.64 | | | >100 | |
| 14 | 23.75 | 1.97 | | | >100 | |
| 15 | 86.55 | 6.13 | 0.672 | 0.33 | >100 | |
| 16 | 28.38 | 0.54 | | | >100 | |
| 17 | 7.44 | 0.34 | | | >100 | |
| 18 | 58.64 | 2.06 | 4.010 | 0.672 | >100 | |
| 19 | 40.52 | 1.65 | | | >100 | |
| 20 | 44.19 | 2.32 | | | >100 | |
| Ibuprofen | 10.01 | 3.46 | | | | |
| Doxorubicin | | | | | 2.281 | 0.019 |

Example 23

Inhibition of A549 NSCLS (Non-Small Cells Lung Cancer) Cell Line

A549 cell lines were obtained from the National Cancer Institute (Cairo, Egypt) and maintained in Roswell Park Memorial Institute medium (RPMI1640) (Invitrogen, Carlsbad, CA, USA) supplemented with 100 mg/mL of streptomycin, 100 units/mL of penicillin and 10% of heat-inactivated fetal bovine serum (Invitrogen) in a humidified, 5% (v/v) $CO_2$ atmosphere at 37° C. The sulforhodamine B (SRB) assays were performed according to Skehan et al 20, 21. Briefly, exponentially growing cells were trypsinized, counted and seeded at the appropriate densities (5000 cells/100 µL/well) into 96-well microtiter plates. Cells were incubated in a humidified atmosphere at 37° C. for 24 h. Then, the cells were exposed to different compounds at the desired concentrations, (0.01, 0.03, 0.1, 0.3, 1, 3, 10, 30 and 100 µM) or to 1% dimethyl sulfoxide (DMSO) for 72 hours. At the end of the treatment period, the media were removed, and the cells were fixed with 10% trichloroacetic acid at 4° C. for 1 h. The cells then were washed with tap water four times and incubated with SRB 0.4% for 30 min. Excess dye was removed by washing repeatedly with 1% (vol/vol) acetic acid. The protein-bound dye was dissolved in 10 mM Tris base solution for OD determination at 510 nm using a SpectraMax plus Microplate Reader (Molecular Devices, CA). Cell viability was expressed relative to the untreated control cells. Statistical analyses were performed using legally licensed GraphPad Prism™ and Instat™ software (GraphPad Inc., La Jolla, CA, USA).

Example 24

Inhibition of A549 NSCLS (Non-Small Cells Lung Cancer) Cell Line

Figure 2:
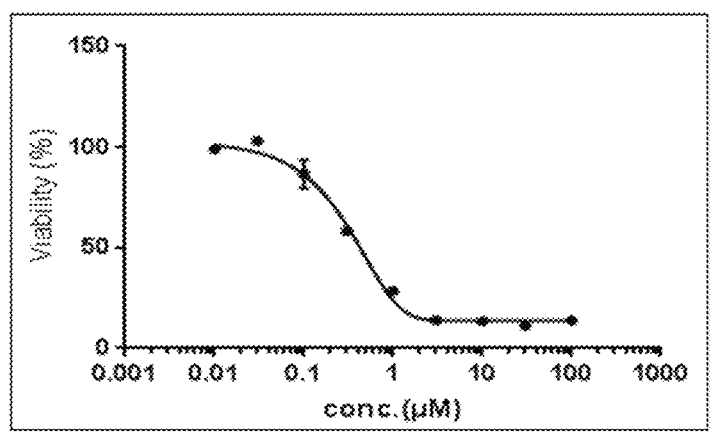
FIG. 2 shows the inhibition of A549 by compound 10 as described herein.

Docking studies were carried out using Glide and other components of Schrödinger Suite. All ligands were converted to 3D structures and prepared using the LigPrep module within the Suite. Standard preparation parameters were used and OPLS3 force field was applied. Possible ionization states at pH 7±2 were generated using Epik. The hFAAH protein crystal structure was downloaded from the protein databank (PDB ID: 3QJ9) and prepared using the Protein Preparation wizard of Schrödinger Suite and standard parameters and OPLS3 force field application. The prepared protein was used to generate two docking grids using the Receptor Grid Generation protocol. One grid contained the active site water molecule and the other lacked this molecule and was used in two different docking experiments. Molecular docking was carried out using Glide using standard parameters. Finally, QikProp tool was used to generate calculated ADME properties of all ligands. QikProp is a pharmacokinetics prediction tool that is able to identify molecular permeability across various membranes and binding to proteins (Schrödinger Release 2020-4: QikProp, Schrödinger, LLC, New York, NY, 2020). Referring to FIG. 2, inhibition of A549 by compound 10 is shown.

It is to be understood that the sulfonylhydrazide derivatives are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A compound having the formula I:

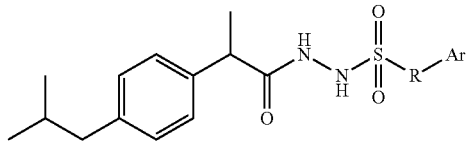

or a pharmaceutically acceptable salt, ester, stereoisomer, or solvate thereof, wherein:
R is a direct bond, —CH$_2$, or —CH$_2$(Br);
Ar is an optionally substituted phenyl, pyridine, naphthalene, or thiophene being optionally substituted with one or more substituents selected from the group consisting of hydrogen, bromine, COCH$_3$, NO$_2$, CF$_3$, OCH$_3$, methyl, isopropyl, and a second optionally substituted phenyl;
wherein the second optionally substituted phenyl is substituted with a hydrogen, methyl, or methoxy.

2. The compound of claim 1, wherein Ar is an optionally substituted pyridine substituted with a CF$_3$.

3. A pharmaceutically acceptable composition comprising a therapeutically effective amount of the compound of claim 1 and a pharmaceutically acceptable carrier.

4. A method of inhibiting FAAH enzyme activity in a patient, comprising administering to a patient in need thereof a therapeutically effective amount of the compound of claim 1.

5. A method of treating a cancer in a patient, comprising administering to a patient in need thereof a therapeutically effective amount of the compound of claim 1, wherein the cancer is lung cancer.

6. A compound selected from the group consisting of:
4-acetyl-N'-(2-(4-isobutylphenyl)propanoyl)benzenesulfonohydrazide (1);
N'-(2-(4-isobutylphenyl) propanoyl)-4-methylbenzene sulfonohydrazide (2);
N'-(2-(4-isobutylphenyl) propanoyl)-2-nitrobenzenesulfonohydrazide (3);
N'-(2-(4-isobutylphenyl)propanoyl)naphthalene-2-sulfonohydrazide (4);
N'-(2-(4-isobutylphenyl) propanoyl)-2, 4, 6 triisopropyl benzene sulfonohydrazide (5);
1-bromo-N'-(2-(4-isobutylphenyl) propanoyl)-1-phenylmethane sulfonohydrazide (6);
N'-(2-(4-isobutylphenyl) propanoyl)-3-(trifluoromethyl) benzene sulfonohydrazide (7);
N'-(2-(4-isobutylphenyl) propanoyl)-4-(trifluoromethyl) benzene sulfonohydrazide (8);
N'-(2-(4-isobutylphenyl) propanoyl) benzenesulfonohydrazide (9);
N'-(2-(4-isobutylphenyl) propanoyl)-[1, 1'-biphenyl]-4-sulfonohydrazide (10);
N'-(2-(4-isobutylphenyl) propanoyl)-4'-methyl-[1, 1'-biphenyl]-4-sulfonohydrazide (11);
N'-(2-(4-isobutylphenyl) propanoyl)-4'-methoxy-[1, 1'-biphenyl]-4sulfonohydrazide (12);
4-Bromo-N'-(2-(4-isobutylphenyl)propanoyl)benzenesulfonohydrazide (13);
N'-(2-(4-isobutylphenyl) propanoyl)-3, 4-dimethoxybenzene sulfonohydrazide (14);
N'-(2-(4-isobutylphenyl)propanoyl)thiophene-2-sulfonohydrazide (15);
5-bromo-N'-(2-(4-isobutylphenyl) propanoyl) thiophene-2-sulfonohydrazide (16);
N'-(2-(4-isobutylphenyl)propanoyl)-5-methylthiophene-2-sulfonohydrazide (17);
N'-(2-(4-isobutylphenyl)propanoyl)pyridine-3-sulfonohydrazide (18);
N'-(2-(4-isobutylphenyl)propanoyl)-6-(trifluoromethyl) pyridine-3sulfonohydrazide (19);
N'-(2-(4-isobutylphenyl)propanoyl)-1-phenylmethanesulfonohydrazide (20); and
a pharmaceutically acceptable salt, ester, stereoisomer, or solvate thereof.

7. A pharmaceutically acceptable composition comprising a therapeutically effective amount of the compound of claim 6 and a pharmaceutically acceptable carrier.

8. A method of treating a cancer in a patient, comprising administering to a patient in need thereof a therapeutically effective amount of the compound of claim 6, wherein the cancer is lung cancer.

* * * * *